US009705570B2

United States Patent
Mroszczak et al.

(10) Patent No.: US 9,705,570 B2
(45) Date of Patent: Jul. 11, 2017

(54) UPDATING GAS DETECTOR CONFIGURATION USING NEAR FIELD COMMUNICATION TAGS

(71) Applicant: Honeywell International Inc., Morristown, NJ (US)

(72) Inventors: Stephen Mroszczak, Calgary (CA); Kirk William Johnson, Calgary (CA); Kelly Englot, Calgary (CA); Mahdi Javer, Calgary (CA)

(73) Assignee: Honeywell International Inc., Morris Plains, NJ (US)

( * ) Notice: Subject to any disclaimer, the term of this patent is extended or adjusted under 35 U.S.C. 154(b) by 0 days.

(21) Appl. No.: 14/825,081

(22) Filed: Aug. 12, 2015

(65) Prior Publication Data

US 2017/0047969 A1    Feb. 16, 2017

(51) Int. Cl.
*H04B 5/00* (2006.01)
*G07C 9/00* (2006.01)
(Continued)

(52) U.S. Cl.
CPC ....... *H04B 5/0056* (2013.01); *G01N 33/0027* (2013.01); *G06F 9/445* (2013.01);
(Continued)

(58) Field of Classification Search
CPC ........... G06K 19/0723; G06K 7/10009; G06K 7/10237; G06K 7/10297; G06K 7/10386; G07C 9/00111
(Continued)

(56) References Cited

U.S. PATENT DOCUMENTS

| 4,525,266 A | 6/1985 | Schmidt et al. |
| 5,068,798 A | 11/1991 | Heath et al. |

(Continued)

FOREIGN PATENT DOCUMENTS

| EP | 2887062 A2 | 6/2015 |
| GB | 2345971 A | 7/2000 |

(Continued)

OTHER PUBLICATIONS

U.S. Appl. No. 14/825,097, Office Action, dated Jun. 2, 2016, 18 pages.

(Continued)

*Primary Examiner* — Carlos E Garcia
(74) *Attorney, Agent, or Firm* — Conley Rose, P.C.; Kristin Jordan Harkins

(57) ABSTRACT

Embodiments relate generally to methods and systems for configuring a gas detector using near-field communication (NFC). A gas detector may be equipped with an NFC reader that will allow the gas detector to scan and read NFC tags. Compatible NFC tags may be acquired and programmed with the configuration settings information. The NFC tag may then be attached to a poster with instructions that show where to place the detector in order to confirm their device's configuration. When the detector is placed in the appropriate location near the tag on the poster, the detector may receive information from the NFC tag, implement the configuration settings, and possibly display a confirmation message to the user. The NFC tag may also be attached to a card carried by a monitor for that work area.

20 Claims, 2 Drawing Sheets

(51) Int. Cl.
*G01N 33/00* (2006.01)
*G06F 9/445* (2006.01)
*G08B 21/02* (2006.01)
*G06K 7/10* (2006.01)

(52) U.S. Cl.
CPC .......... *G07C 9/00111* (2013.01); *G08B 21/02* (2013.01); *G06K 7/10386* (2013.01)

(58) Field of Classification Search
USPC ............................................ 340/10.51, 572.1
See application file for complete search history.

(56) References Cited

U.S. PATENT DOCUMENTS

| | | | |
|---|---|---|---|
| 5,468,968 A | 11/1995 | Bailey et al. | |
| 6,720,866 B1* | 4/2004 | Sorrells | G06K 19/0717 340/10.34 |
| 6,809,646 B1 | 10/2004 | Lee | |
| 7,397,370 B2* | 7/2008 | Bratkovski | G01D 21/00 340/333 |
| 7,782,224 B2 | 8/2010 | Marchetti | |
| 8,618,914 B2* | 12/2013 | Bachman | G06K 19/0702 338/13 |
| 8,624,725 B1* | 1/2014 | MacGregor | H04W 4/026 340/539.13 |
| 2001/0040512 A1* | 11/2001 | Hines | G07C 9/00111 340/8.1 |
| 2002/0190866 A1* | 12/2002 | Richardson | A62B 7/00 340/632 |
| 2005/0088299 A1* | 4/2005 | Bandy | G08B 25/10 340/539.16 |
| 2007/0013516 A1* | 1/2007 | Freitag | G01S 1/68 340/572.1 |
| 2007/0052540 A1* | 3/2007 | Hall | G08B 13/24 340/572.1 |
| 2008/0030324 A1* | 2/2008 | Bekritsky | H04B 5/0056 340/539.22 |
| 2008/0101400 A1* | 5/2008 | Auterinen | H04L 12/66 370/463 |
| 2008/0159547 A1 | 7/2008 | Schuler et al. | |
| 2008/0231836 A1* | 9/2008 | Curello | H01M 8/04201 356/72 |
| 2009/0058635 A1 | 3/2009 | LaLonde et al. | |
| 2009/0058648 A1* | 3/2009 | Tuttle | G08B 7/066 340/572.1 |
| 2009/0091465 A1 | 4/2009 | Buckingham et al. | |
| 2009/0184165 A1* | 7/2009 | Bertness | H01M 2/0267 235/462.01 |
| 2009/0231099 A1 | 9/2009 | Hyde et al. | |
| 2010/0241464 A1 | 9/2010 | Amigo et al. | |
| 2011/0037599 A1 | 2/2011 | Johnson, Jr. et al. | |
| 2011/0043373 A1* | 2/2011 | Best | G01S 1/68 340/8.1 |
| 2012/0007736 A1* | 1/2012 | Worthington | G08B 17/117 340/539.22 |
| 2012/0063956 A1 | 3/2012 | Truex et al. | |
| 2012/0161967 A1* | 6/2012 | Stern | G06K 7/10366 340/572.1 |
| 2013/0002405 A1 | 1/2013 | Pesonen et al. | |
| 2013/0244615 A1* | 9/2013 | Miller | H04W 12/06 455/411 |
| 2014/0293306 A1 | 10/2014 | Tredoux et al. | |
| 2014/0336920 A1* | 11/2014 | Burrell | G01C 21/206 701/409 |
| 2014/0349707 A1* | 11/2014 | Bang | H04Q 9/00 455/556.1 |
| 2015/0102926 A1 | 4/2015 | Kamalakannan et al. | |
| 2015/0116093 A1* | 4/2015 | Swager | G06K 19/0716 340/10.4 |
| 2015/0269818 A1* | 9/2015 | Jain | G08B 13/248 340/572.1 |

FOREIGN PATENT DOCUMENTS

| | | |
|---|---|---|
| WO | 9207261 A1 | 4/1992 |
| WO | 2012006090 A2 | 1/2012 |
| WO | 2013185821 A1 | 12/2013 |

OTHER PUBLICATIONS

U.S. Appl. No. 14/825,097, Final Office Action, dated Sep. 14, 2016, 18 pages.
U.S. Appl. No. 14/825,097, Notice of Allowance, dated Dec. 2, 2016, 16 pages.
PCT Application No. PCT/US2016/012942, International Search Report, dated Apr. 5, 2016, 4 pages.
PCT Application No. PCT/US2016/012942, Written Opinion of the International Searching Authority, dated Apr. 5, 2016, 5 pages.
Europe Patent Application No. 16182897.5, Extended European Search Report, dated Nov. 21, 2016, 11 pages.
Whitson Gordon: "How to Automate Your Phone for Every Room in the House with NFC Tags", Lifehacker, Apr. 16, 2013, Retrieved from the Internet: http://lifehacker.com/how-to-automate-your-phone-for-every-room-in-the-house-473409962, retrieved on Jun. 23, 2015, 6 pages.
Europe Patent Application No. 16182884.3 Extended European Search Report, dated Dec. 15, 2016, 8 pages.

* cited by examiner

UPDATING GAS DETECTOR CONFIGURATION USING NEAR FIELD COMMUNICATION TAGS

CROSS-REFERENCE TO RELATED APPLICATIONS

Not applicable.

STATEMENT REGARDING FEDERALLY SPONSORED RESEARCH OR DEVELOPMENT

Not applicable.

REFERENCE TO A MICROFICHE APPENDIX

Not applicable.

BACKGROUND

In hazardous work environments, user may carry gas detectors with them as they work, to allow for detection of gas exposure. The gas detector may alert the user if an exposure limits are reached while the user is wearing the gas detector. Gas detectors may comprise interfaces for communicating with the user, such as displays, lights, buzzers, and input buttons. Gas detectors may be configured with settings for alarms, exposure limits, display settings, light and buzzer settings, etc.

SUMMARY

Aspects of the disclosure may include embodiments of a method for updating the settings of a gas detector for a particular work area, when the user is entering the work area, the method comprising providing a gas detector comprising an near-field communication (NFC) reader; programming an NFC tag with settings information for the gas detector, wherein the NFC tag is located at the entry of the work area; placing the gas detector in proximity to the NFC tag; receiving, by the gas detector, settings information from the NFC tag; updating the settings on the gas detector based on the received settings information; and displaying a confirmation message to the user when the new settings have been applied.

In some embodiments, the method may further comprise receiving, by the gas detector, a work area identifier from the NFC tag; and storing the work area identifier by the gas detector. In some embodiments, the NFC tag is located on a poster, wherein the poster contains instructions for the user and indicates the location of the NFC tag. In some embodiments, the NFC tag is located on a card carried by a monitor for the work area. In some embodiments, the settings information comprises alarm settings and exposure limits. In some embodiments, the method may further comprise repeating the steps of the method at every new work area entered by the user. In some embodiments, the method may further comprise placing the gas detector in proximity to a second NFC tag, wherein the second NFC tag is at the entry of a second work area; receiving, by the gas detector, second settings information from the second NFC tag; updating the settings on the gas detector based on the received second settings information; and displaying a confirmation message to the user when the new settings have been applied.

Other aspects of the disclosure may include embodiments of a method for updating the settings of a gas detector for a particular work area, when the user is entering the work area, the method comprising providing a gas detector comprising an near-field communication (NFC) reader; programming an NFC tag with settings information for the gas detector, wherein the NFC tag is located at the entry of the work area; placing the gas detector in proximity to the NFC tag; receiving, by the gas detector, settings information from the NFC tag; updating the settings on the gas detector based on the received settings information; displaying a confirmation message to the user when the new settings have been applied; receiving, by the gas detector, a work area identifier from the NFC tag; and storing, by the gas detector, the work area identifier.

In some embodiments, the method may further comprise placing the gas detector in proximity to a second NFC tag, wherein the second NFC tag is at the entry of a second work area; receiving, by the gas detector, second settings information from the second NFC tag; updating the settings on the gas detector based on the received second settings information; displaying a confirmation message to the user when the new settings have been applied; receiving, by the gas detector, a second work area identifier for the second work area from the NFC tag; and storing, by the gas detector, the second work area identifier. In some embodiments, the method may further comprise repeating the steps of the method at every new work area entered by the user. In some embodiments, the method may further comprise tracking the location of a worker based on the work area identifiers that are stored by the gas detector. In some embodiments, the NFC tag may be located on a poster or sign located at the entry of a work area, wherein the poster contains instructions for the user and draws attention to the NFC tag. In some embodiments, the NFC tag is located on a card carried by a monitor for the work area.

Additional aspects of the disclosure may include embodiments of a gas detector system comprising a NFC tag that is operable to store settings information for gas detectors, wherein the NFC tag is located at the entry to a work area; a gas detector, wherein the gas detector is operable to detect gas levels in the environment and provide alerts, alarms, and other indications to a user, and wherein the gas detector comprises: an NFC reader operable to communicate with the NFC tag; a user interface; and a processor and storage operable to receive settings information from the NFC tag; update the settings of the gas detector accordingly; receive a work area identifier from the NFC tag; and store the work area identifier.

In some embodiments, the gas detector comprises a single button for input from a user to the gas detector. In some embodiments, the gas detector comprises one or more buttons for input from a user to the gas detector. In some embodiments, the gas detector is operable to communicate with a second NFC tag located at the entry to a second work area, receive second settings information from the second NFC tag, and update the settings of the gas detector accordingly. In some embodiments, the settings information comprises alarm settings and exposure limits. In some embodiments, the user interface of the gas detector comprises a display, and wherein the gas detector displays a confirmation message for the user when the settings of the gas detector have been updated. In some embodiments, the NFC tag is located on a poster, wherein the poster contains instructions for the user and indicates the location of the NFC tag.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief descrip

DETAILED DESCRIPTION

Figure 1:
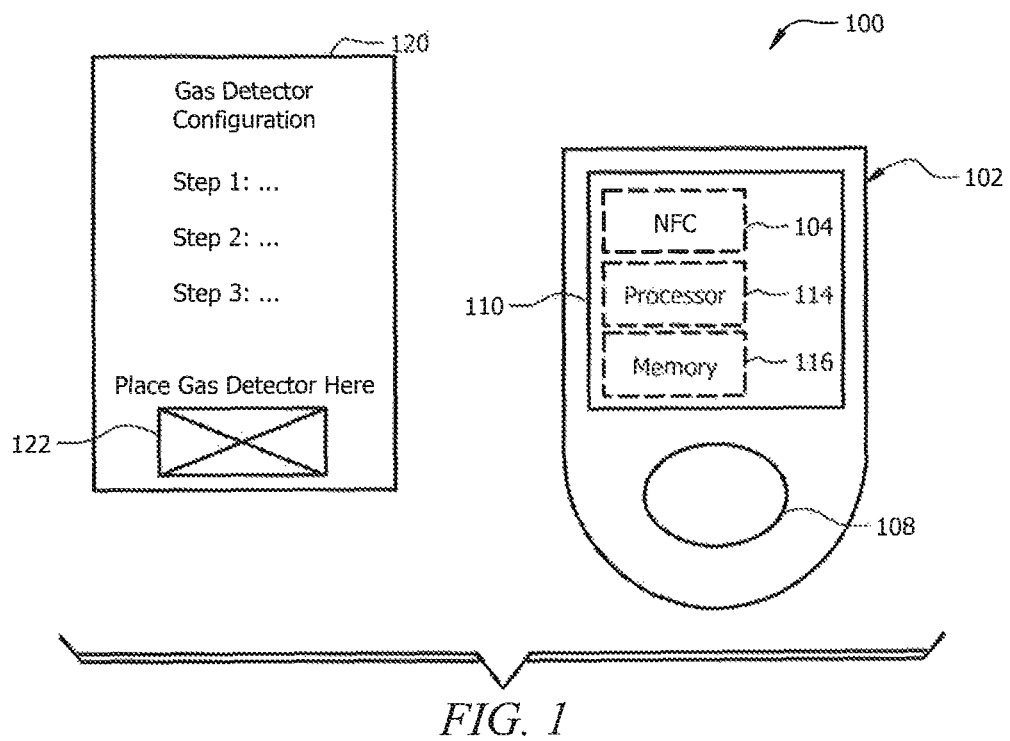
- FIG. 1 illustrates a gas detector system according to an embodiment of the disclosure.

It should be understood at the outset that although illustrative implementations of one or more embodiments are illustrated below, the disclosed systems and methods may be implemented using any number of techniques, whether currently known or not yet in existence. The disclosure should in no way be limited to the illustrative implementations, drawings, and techniques illustrated below, but may be modified within the scope of the appended claims along with their full scope of equivalents.

The following brief definition of terms shall apply throughout the application:

The term "comprising" means including but not limited to, and should be interpreted in the manner it is typically used in the patent context;

The phrases "in one embodiment," "according to one embodiment," and the like generally mean that the particular feature, structure, or characteristic following the phrase may be included in at least one embodiment of the present invention, and may be included in more than one embodiment of the present invention (importantly, such phrases do not necessarily refer to the same embodiment);

If the specification describes something as "exemplary" or an "example," it should be understood that refers to a non-exclusive example;

The terms "about" or approximately" or the like, when used with a number, may mean that specific number, or alternatively, a range in proximity to the specific number, as understood by persons of skill in the art field; and If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

Embodiments of the disclosure include methods and systems for configuring a gas detector using NFC. Gas detectors are portable devices that are carried by a user while working in potentially hazardous environments. As such, a user may carry the same gas detector with them to each work area that user goes to during a work day. When a user is entering a work area, the gas detector may or may not be configured with the correct settings for that area. The settings may include alarms and set points (or limits). Typically, these settings changes would need to be made at a computer or docking station, but unless the onsite policy forces the user to check the gas detector settings before entering a work area, the gas detector may be used with the wrong settings for that area. In order to confirm the settings for a particular work area, a user would need to know what the correct settings are, know how to check the settings on the device, and know how to change the settings if they are wrong. If a gas detector is used with incorrect settings, a user may be in danger of hazardous gas exposure that may not be indicated by the gas detector.

To simplify this process, and help ensure that gas detectors are being used with the correct settings, Applicants have proposed a system using gas detectors equipped with an NFC reader. Additionally, each work area would have an NFC tag programmed with the configuration settings for that particular area, wherein the NFC tag may be displayed in prominent areas near the entry points of the work area. In some embodiments, the NFC tag may be embedded in a poster with easy to understand instructions that would draw the attention of a user, reminding them to update the settings of their device. When the gas detector is brought within the range of the NFC tag, the NFC reader of the gas detector may receive configuration information, and then update the configuration of the gas detector as needed. In addition, the data stored on the tag could be encrypted and authenticated so that it could not be tampered with or changed by unauthorized personnel.

A gas detector may be equipped with an NFC reader that will allow the gas detector to scan and read NFC tags. Compatible NFC tags may be acquired and programmed with the configuration settings information. The NFC tag may then be attached to a poster with instructions that show where to place the detector in order to confirm their device's configuration. When the detector is placed in the appropriate location near the tag on the poster, the detector may receive information from the NFC tag, implement the configuration settings, and possibly display a confirmation message to the user.

Referring now to FIG. 1, an exemplary embodiment of the system 100 is described. The system may comprise a gas detector 102, wherein the gas detector 102 comprises an NFC reader 104. The gas detector 102 may comprise any type of gas detector operable to detect gas levels in the environment and provide alerts, alarms, and other indications to a user. In some embodiments, the gas detector 102 may be operable to communicate with a central monitoring station. In some embodiments, the gas detector 102 may comprise wireless communication capabilities.

The gas detector may comprise a user interface 110 operable to interact with a user, wherein the user interface may comprise a display, one or more light, and one or more buzzers, as well as other indicators. Additionally, in some embodiments, the gas detector 102 may comprise a single button 108 for input from a user to the gas detector 102. In some embodiments, the gas detector 102 may comprise multiple buttons 108 for input from a user.

The system 100 may also comprise a poster or sign 120, wherein the poster 120 comprises an NFC tag 122 attached to a portion of the poster 120. The poster 120 may be placed at an entry point for a work area, wherein the work area requires specific gas detector settings. The settings information may be stored on the NFC tag 121. The settings may comprise alarms, exposure limits, display settings, light and buzzer settings, bump and calibration intervals, confidence and IntelliFlash indicator interval, and instrument lockout conditions. In some embodiments, the NFC tag may also communicate with an identifier for the work area.

The gas detector 102 may comprise a processor 114 and storage 116 for receiving settings information via NFC and implementing the settings as necessary. In some embodiments, the settings information may also be stored by the storage 116 of the gas detector. In some embodiments, the settings information may comprise indicators for the type of information. For example, the data format may be "parameter=value," wherein the processor 114 may direct the information as indicated by the parameter indicator. When the gas detector 102 receives the settings information from the NFC tag 122, the processor 114 may automatically implement the settings on the gas detector 102. In some embodiments, the gas detector 102 may indicate to a user when the settings have been updated, such as with a displayed message. This step may be programmed into the instructions stored by the NFC tag, or may be built into the processor 114 of the gas detector.

The use of NFC to associate a user with a gas detector may also be useful for providing quick way to ensure the configuration settings of a gas detector are correct when a user is entering a new work area, without required the user to take the gas detector out of service, connect to a docking station or computer, or any other time consuming activity. A user may update the settings of the gas detector 102 as much as needed during the use of the gas detector 102, wherein at each new work area, the user may simply communicate with the new NFC tag 122 at the entry of the new work area to ensure that the settings are correct.

Figure 2:
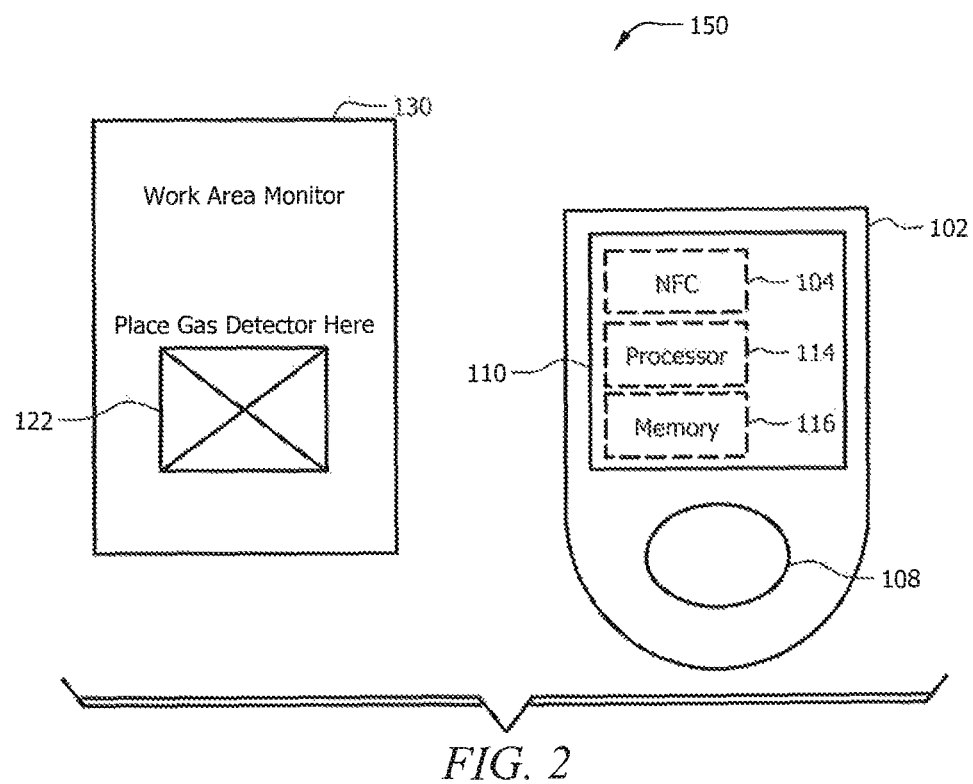
FIG. 2 illustrates another gas detector system according to an embodiment of the disclosure.

FIG. 2 illustrates another exemplary system 150 of the disclosure, wherein the NFC tag 122 is attached to a card 130 carried by a work area monitor. The work area monitor may be in charge of monitoring entry to the work area, and may also be in charge of ensuring that workers entering the work area are carrying gas detectors with the correct configuration settings. Similar to the system 100 of FIG. 1, the gas detector 102 may be placed in proximity to the NFC tag 122 of the card 130, wherein settings information may be received by the NFC reader of the gas detector 102 from the NFC tag 122. The settings information may then be implemented by the gas detector 102, as described above.

In some embodiments, a facility may comprise multiple work areas with different requirements. Some work areas may have posters installed with NFC tags containing gas detector settings information, while some other work areas may have monitors at the entry of the work area carrying a card to communicate gas detector settings information. Any combination of these embodiments may be used in a facility.

Figure 3:
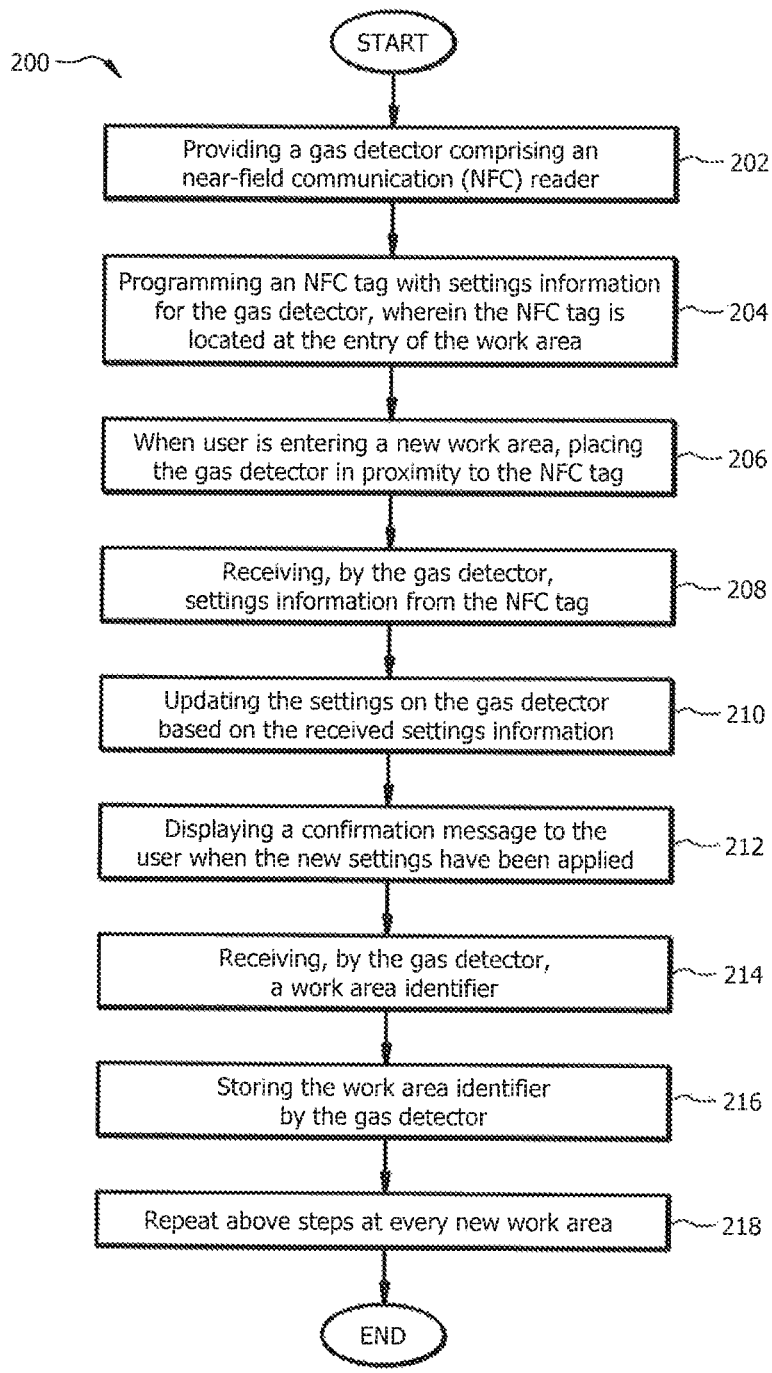
FIG. 3 illustrates a method for updating the settings of a gas detector for a particular work area according to an embodiment of the disclosure.

FIG. 3 shows an exemplary method 200 for ensuring the settings of a gas detector are correct and updating the settings of a gas detector for a particular worksite. At step 202, a gas detector is provided comprising an near-field communication (NFC) reader. At step 204, an NFC tag is programmed with settings information for the gas detector, wherein the NFC tag is located at the entry of the work area. At step 206, when user is entering a new work area, the gas detector is placed in proximity to an NFC tag. In some embodiments, the NFC tag may be located on a poster or sign, wherein the poster contains instructions for the user and draws attention to the NFC tag. In some embodiments, the NFC tag may be attached to a card carried by a work area monitor. In some embodiments, settings information may be stored on the NFC tag.

At step, 208, the gas detector may receive the settings information from the NFC tag. At step 210, the gas detector may update the settings on the gas detector based on the received settings information. In some embodiments, the settings information may comprise alarm settings and exposure limits. At step 212, the gas detector may display a confirmation message to the user when the new settings have been applied. In some embodiments, at step 214, the gas detector may also receive an identifier for the work area from the NFC tag, and at step 216, the gas detector may store the work area identifier. At step 218, the above steps may be repeated every time a user enters a new work area.

While various embodiments in accordance with the principles disclosed herein have been shown and described above, modifications thereof may be made by one skilled in the art without departing from the spirit and the teachings of the disclosure. The embodiments described herein are representative only and are not intended to be limiting. Many variations, combinations, and modifications are possible and are within the scope of the disclosure. Alternative embodiments that result from combining, integrating, and/or omitting features of the embodiment(s) are also within the scope of the disclosure. Accordingly, the scope of protection is not limited by the description set out above, but is defined by the claims which follow, that scope including all equivalents of the subject matter of the claims. Each and every claim is incorporated as further disclosure into the specification and the claims are embodiment(s) of the present invention(s). Furthermore, any advantages and features described above may relate to specific embodiments, but shall not limit the application of such issued claims to processes and structures accomplishing any or all of the above advantages or having any or all of the above features.

Additionally, the section headings used herein are provided for consistency with the suggestions under 37 C.F.R. 1.77 or to otherwise provide organizational cues. These headings shall not limit or characterize the invention(s) set out in any claims that may issue from this disclosure. Specifically and by way of example, although the headings might refer to a "Field," the claims should not be limited by the language chosen under this heading to describe the so-called field. Further, a description of a technology in the "Background" is not to be construed as an admission that certain technology is prior art to any invention(s) in this disclosure. Neither is the "Summary" to be considered as a limiting characterization of the invention(s) set forth in issued claims. Furthermore, any reference in this disclosure to "invention" in the singular should not be used to argue that there is only a single point of novelty in this disclosure. Multiple inventions may be set forth according to the limitations of the multiple claims issuing from this disclosure, and such claims accordingly define the invention(s), and their equivalents, that are protected thereby. In all instances, the scope of the claims shall be considered on their own merits in light of this disclosure, but should not be constrained by the headings set forth herein.

Use of broader terms such as comprises, includes, and having should be understood to provide support for narrower terms such as consisting of, consisting essentially of, and comprised substantially of. Use of the term "optionally," "may," "might," "possibly," and the like with respect to any element of an embodiment means that the element is not required, or alternatively, the element is required, both alternatives being within the scope of the embodiment(s). Also, references to examples are merely provided for illustrative purposes, and are not intended to be exclusive.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. A method for updating the settings of a gas detector for a particular work area, when the user is entering the work area, the method comprising:
    providing a gas detector comprising a near-field communication (NFC) reader and memory storing initial settings, wherein the initial settings comprise alarm settings and exposure limits associated with gas detection, wherein the gas detector is configured to detect gas levels with the initial settings associated with gas detection;
    programming an NFC tag with settings information associated with gas detection in the work area for use by the gas detector, wherein the NFC tag is located at the entry of the work area;
    placing the NFC reader of the gas detector in proximity to the NFC tag that comprises the settings information associated with the work area, wherein the settings information comprises updated alarm settings and updated exposure limits for gas detection in the work area;
    in response to placing the NFC reader of the gas detector in proximity to the NFC tag:
        receiving, by the NFC reader of the gas detector, the settings information associated with the work area from the NFC tag;
        based on receiving the settings information from the NFC tag, updating, by the gas detector, the gas detector to detect gas levels with the settings information for the work area received from the NFC tag instead of with the initial settings, wherein the gas detector detects gas levels based on the updated alarm settings and updated exposure limits of the settings information received from the NFC tag;
    displaying, by the gas detector, a confirmation message to the user when the as detector has been updated to use the setting information for the work area; and
    detecting, by the gas detector, gas levels in the work area in accordance with the settings information received from the NFC tag.

2. The method of claim 1 further comprising:
    receiving, by the gas detector from the NFC tag, a work area identifier in response to placing the NFC reader of the gas detector in proximity to the NFC tag; and
    storing, by the gas detector, the work area identifier on the gas detector.

3. The method of claim 1, wherein the NFC tag is located on a poster, wherein the poster contains instructions for the user and indicates the location of the NFC tag.

4. The method of claim 1, wherein the NFC tag is located on a card carried by a monitor for the work area.

5. The method of claim 1, wherein the alarm settings and exposure limits of the initial settings are incorrect for the work area, and wherein the initial settings on the gas detector are updated to the settings information for the work area.

6. The method of claim 1 further comprising receiving and changing settings by the gas detector from an NFC tag at every new work area entered by the user based on the NFC reader of the gas detector being placed in proximity to the NFC tag at the new work area.

7. The method of claim 1 further comprising:
    placing the gas detector in proximity to a second NFC tag, wherein the second NFC tag is at the entry of a second work area and comprises different settings information associated with the second work area, the different settings information being different from the initial settings and the settings information for the work area;
    in response to placing the NFC reader of the gas detector in proximity to the second NFC tag associated with the second work area:
        receiving, by the NFC reader of the gas detector, the second settings information from the second NFC tag associated with the second work area;
        updating, by the gas detector, from the settings information for the work area on the gas detector to the second settings information associated with the second work area based on the received second settings information; and
    displaying by the gas detector, a confirmation message to the user when the gas detector has changed to the second settings information for the second work area received by the NFC tag of the second work area.

8. A method for updating the settings of a gas detector for a particular work area, when the user is entering the work area the method comprising:
    providing a gas detector comprising a near-field communication (NFC) reader and memory storing initial settings, wherein the initial settings comprise alarm settings and exposure limits associated with gas detection, wherein the gas detector is configured for gas detection with the initial settings associated with gas detection;
    programming an NFC tag with settings information associated with gas detection in the work area for use by the gas detector, wherein the NFC to is located at the entry of the work area;
    placing the NFC reader of the gas detector in proximity to the NFC tag having the settings information associated with the work area, wherein the settings information comprises updated alarm settings and updated exposure limits for gas detection in the work area;
    in response to placing the NFC reader of the gas detector in proximity to the NFC tag:
        receiving, by the gas detector, a work area identifier for the work area and settings information associated with gas detection in the work area from the NFC tag;
        updating, by the gas detector, the gas detector to detect gas levels with the settings information associated with the work area received from the NFC tag instead of with the initial settings, wherein the as detector detects gas levels based on the updated alarm settings and updated exposure limits of the settings information received from the NFC tag;
        storing, by the gas detector, the work area identifier from the NIT tag; and
    detecting, by the gas detector, gas levels in the work area in accordance with the settings information that were updated on the gas detector.

9. The method of claim 8 further comprising:
    placing the gas detector in proximity to a second NFC tag associated with a second work area, wherein the second NFC tag is at the entry of the second work area and comprises second settings information about gas detection in the second work area for use by gas detectors;

receiving, by the gas detector, second settings information from the second NFC tag;

in response to receiving the second settings information from the second NFC tag, updating the gas detector from the settings information associated with the first work area to second settings information from the second NFC tag associated with the second work area based on the received second settings information;

receiving, by the gas detector, a second work area identifier for the second work area from the second NFC tag in response to the gas detector being in proximity to the second NFC tag; and storing and updating, by the gas detector, the gas detector with the second work area identifier received from the second NFC tag.

10. The method of claim 8 further comprising receiving and changing settings by the gas detector front an NFC tag at every new work area entered by the user based on the NFC reader of the gas detector being placed in proximity to the NFC tag at the new work area.

11. The method of claim 8 further comprising tracking the location of a worker based on the work area identifiers that are stored by the gas detector.

12. The method of claim 8, wherein the NFC tag is located on a poster or sign located at the entry of a work area, wherein the poster contains instructions for the user and draws attention to the NFC tag.

13. The method of claim 8, wherein the NFC tag is located on a card carried by a monitor for the work area.

14. A gas detector system comprising:

a near-field communication (NFC) tag that stores settings information associated with a work area for use by gas detectors, wherein the NFC tag is located at the entry to the work area;

a gas detector, wherein the gas detector is operable to detect gas levels in the environment and provide alerts and alarms to a user, and wherein the gas detector comprises:

an NFC reader operable to communicate with at least the NFC tag;

a user interface; and a processor and storage communicatively coupled to the NFC reader and configured such that the processor:

stores initial settings for detection of gas levels, wherein the initial settings comprise alarm settings and exposure limits associated with gas detection by the gas detector;

in response to the NFC reader being in proximity to the NFC tag:

receives, from the NFC tag, a work area identifier and settings information associated with the work area, wherein the settings information comprises updated alarm settings and updated exposure limits for gas detection in the work area;

updates the gas detector to detect gas levels with the settings information associated with the work area received from the NFC tag instead of with the initial settings;

stores the work area identifier received from the NFC tag; and detects gas levels in the work area based on the updated alarm settings and updated exposure limits of the settings information updated on the gas detector that were received from the NFC tag.

15. The system of claim 14, wherein the gas detector comprises a single button for input from a user to the gas detector.

16. The system of claim 14, wherein the gas detector comprises one or more buttons for input from a user to the gas detector.

17. The system of claim 14, wherein the gas detector is operable to communicate with a second NFC tag located at the entry to a second work area, receive second settings information from the second NFC tag, and update the settings of the gas detector accordingly.

18. The system of claim 14, wherein the alarm settings and exposure limits of the initial setting are incorrect for the work area, and wherein the initial settings on the gas detector are updated to the settings information for the work area.

19. The system of claim 14, wherein the user interface of the gas detector comprises a display, and wherein the gas detector displays a confirmation message for the user when the settings of the gas detector have been updated.

20. The system of claim 14, wherein the NFC tag is located on a poster, wherein the poster contains instructions for the user and indicates the location of the NFC tag.

* * * * *

UNITED STATES PATENT AND TRADEMARK OFFICE
CERTIFICATE OF CORRECTION

PATENT NO. : 9,705,570 B2
APPLICATION NO. : 14/825081
DATED : July 11, 2017
INVENTOR(S) : Stephen Mroszczak et al.

It is certified that error appears in the above-identified patent and that said Letters Patent is hereby corrected as shown below:

In the Specification

Column 4, Line 55: "121" should be "122"

Column 4, Line 58: "interval" should be "intervals"

In the Claims

Column 7, Line 47 Claim 1: "as" should be "gas"

Column 8, Line 30 Claim 8: insert a --,-- after "area"

Column 8, Line 39 Claim 8: "to" should be "tag"

Column 8, Line 55 Claim 8: "as" should be "gas"

Column 8, Line 60 Claim 8: "NIT" should be "NFC"

Column 9, Line 19 Claim 10: "front" should be "from"

Column 10, Line 36 Claim 18: "setting" should be "settings"

Signed and Sealed this
Twenty-first Day of November, 2017

Joseph Matal
*Performing the Functions and Duties of the
Under Secretary of Commerce for Intellectual Property and
Director of the United States Patent and Trademark Office*